(12) United States Patent
Komata et al.

(10) Patent No.: US 7,544,844 B2
(45) Date of Patent: Jun. 9, 2009

(54) PROCESS FOR PRODUCING 3,3,3-TRIFLUOROPROPIONALDEHYDE

(75) Inventors: Takeo Komata, Kawagoe (JP); Kenji Hosoi, Kasukabe (JP); Shinya Akiba, Fujimino (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 12/065,299

(22) PCT Filed: Sep. 12, 2006

(86) PCT No.: PCT/JP2006/318048

§ 371 (c)(1),
(2), (4) Date: Feb. 29, 2008

(87) PCT Pub. No.: WO2007/037119

PCT Pub. Date: Apr. 5, 2007

(65) Prior Publication Data

US 2009/0105506 A1    Apr. 23, 2009

(30) Foreign Application Priority Data

Sep. 29, 2005    (JP) .............................. 2005-284802

(51) Int. Cl.
C07C 45/42    (2006.01)
C07C 43/00    (2006.01)
(52) U.S. Cl. .................. 568/485; 568/488; 568/681
(58) Field of Classification Search .............. 568/485, 568/488, 681
See application file for complete search history.

(56) References Cited

U.S. PATENT DOCUMENTS

| 2,715,144 | A | 8/1955 | Ruh |
| 5,777,184 | A | 7/1998 | Van Der Puy et al. |
| 6,111,139 | A | 8/2000 | Van Der Puy |

2003/0114721 A1    6/2003  Roques

FOREIGN PATENT DOCUMENTS

| JP | 63-63633 A | 3/1988 |
| JP | 2001-302582 A | 10/2001 |
| JP | 2003-522743 A | 7/2003 |
| JP | 2004-155676 A | 6/2004 |

OTHER PUBLICATIONS

B.T. Golding et al., "3,3,3-Trifluoropropan-1-ol and 3,3,3-Trifluoropropanal" Journal of Fluorine Chemistry, 1985, pp. 153-158, vol. 30, Elsevier Sequoia, The Netherlands.
S.V. Pazenok et al., "β-Perfluoroalkylvinyl Alkyl Ethers", Zhurnal Organicheskoi Khimii, Jul. 1989, pp. 1238-1240 (1376-1380), vol. 25, No. 7, Plenum Publishing Corporation.
A.V. Popov et al., "Reaction of N- (3,3,3-Trifluoro-2-Trifluoromethylprop-1-enyl)Dimethylamine with $MgSO_4 \cdot 7H_2O$. Synthesis of 4,4-Difluoro-5-Trifluoromethyl-2-(2,2,2-Trifluoro-1-Trifluoromethylethyl)-4H-1,3-Dioxine and Cis/ Trans-3-Dimethylamino-2-Trifluoromethacryloyl Fluoride", Russian Chemical Bulletin/ Izvestiya Akademii Nauk, May 1997, pp. 1032-1033 (1069-1071), vol. 46, No. 5, Plenum Publishing Corporation, Russia.
International Search Report dated Oct. 24, 2006 with English translation of relevant portion (Three (3) pages).

*Primary Examiner*—Sikarl A Witherspoon
(74) *Attorney, Agent, or Firm*—Crowell & Moring LLP

(57) ABSTRACT

There is provided a process for producing 3,3,3-trifluoropropionaldehyde, including the step of hydrolyzing a benzyl vinyl ether of the formula [1] in the presence of a catalyst selected from the group consisting of Arrhenius acids and Lewis acids,

[Chem. 17]

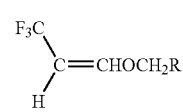

[1]

where R represents phenyl or phenyl having a substituent $R^1$ selected from the group consisting of alkyl groups, alkoxy groups, halogen atoms, nitro groups and amino groups.

9 Claims, No Drawings

PROCESS FOR PRODUCING 3,3,3-TRIFLUOROPROPIONALDEHYDE

BACKGROUND OF THE INVENTION

The present invention relates to a process for producing 3,3,3-trifluoropropionaldehyde which is useful as intermediates for medical drugs and agricultural chemicals and as raw materials or synthetic intermediates for high-performance materials such as fluorine-containing polymers.

There are various reports made about the techniques for production of 3,3,3-trifluoropropionaldehyde.

Non-Patent Publication 1 discloses a process of producing 3,3,3-trifluoropropionaldehyde by converting 3,3,3-trifluoropropene into 3,3,3-trifluoro-1-propanol with the use of mercury (II) nitrate and glacial acetic acid, and then, oxidizing the 3,3,3-trifluoro-1-propanol with sodium chromate. Patent Publication 2 discloses a process of producing 3,3,3-trifluoropropionaldehyde by reacting 3,3,3-trifluoropropene with water in the presence of a palladium salt. Non-Patent Publication 2 discloses a process of producing 3,3,3-trifluoropropionaldehyde by adding trifluoromethyl iodide to ethyl vinyl ether and hydrolyzing the resulting addition product. Patent Publication 3 discloses a process of producing 3,3,3-trifluoropropionaldehyde by converting 1-chloro-3,3,3-trifluoropropene to 3,3,3-trifluoropropenyl acetate with the use of a palladium salt, sodium acetate and glacial acetic acid, and then, hydrolyzing the 3,3,3-trifluoropropenyl acetate.

Patent Publication 4 discloses a process of producing 3,3,3-trifluoropropionaldehyde by hydrolyzing alkyl 3,3,3-trifluoropropenyl ether with the use of an aqueous hydriodic acid solution.

Patent Publication 5 discloses a process of producing 3,3,3-trifluoropropionaldehyde by reacting 1-chloro-3,3,3-trifluoropropene with metal alkoxide in an alcohol (ROH) where R has a carbon number of 1 to 4, thereby obtaining $CF_3CH=CHOR$ or $CF_3CH(OR)_2$ as a reaction product, and then, hydrolyzing the reaction product in the presence of an alkane acid having a carbon number of 3 to 13. Patent Publication 1 discloses a process of producing 3,3,3-trifluoropropionaldehyde by adding trifluoromethanesulfonyl chloride to vinyl chloride, thereby obtaining 1-chloro-3,3,3-trifluoropropylacetate, and then, hydrolyzing the 1-chloro-3,3,3-trifluoropropylacetate with sulfuric acid.

Non-Patent Publication 3 discloses a process of producing 3,3,3-trifluoropropionaldehyde by reacting dimethyl-[1-(2-trifluoromethyl-3,3,3-trifluoropropenyl)]amine, which is one kind of trifluoromethyl-containing enamine, for 28 days in the presence of a magnesium sulfate hydrate.

[Patent Publication 1] Published Japanese Translation of PCT Application No. 2003-522743
[Patent Publication 2] Japanese Laid-Open Patent Publication No. 6363633
[Patent Publication 3] U.S. Pat. No. 5,777,184
[Patent Publication 4] U.S. Pat. No. 2,715,144
[Patent Publication 5] U.S. Pat. No. 6,111,139
[Non-Patent Publication 1] Journal of Fluorine Chemistry, Vol. 30, Pages 153-158, 1985 (Netherlands)
[Non-patent Publication 2] Zhurnal Organicheskoi Khimii, Vol. 25, No. 7, Pages 1376-1380, 1989 (Soviet)
[Non-Patent Publication 3] Izvestiya Akademii Nauk, Seriya Khimicheskaya, Vol. 5, Pages 1069-1071, 1997 (Russia)

SUMMARY OF THE INVENTION

However, the process of Non-Patent Publication 1 uses toxic agents such as mercury and chromic acid. Each of the processes of Patent Publications 2 and 3 requires a large amount of expensive palladium salt. The process of Non-Patent Publication 2 also uses expensive trifluoromethyl iodide. The process of Patent Publication 4 uses highly-corrosive, hard-to-handle hydriodic acid during the hydrogenolysis and generates an equivalent molar amount of alkyl iodide (such as methyl iodide) as an undesired byproduct with respect to the target 3,3,3-trifluoropropionaldehyde. The process of Patent Publication 1 requires expensive trifluoromethanesulfonyl chloride. The process of Patent Publication 3 is a rare reaction example of converting trifluoromethyl-containing enamine to 3,3,3-trifluoropropionaldehyde, but presents problems that it takes 28 days to carry out such a conversion reaction and that the 3,3,3-trifluoropropionaldehyde is not a main reaction product.

On the other hand, the process of Patent Publication 5 is common to the present invention, in that: the 3,3,3-trifluoropropionaldehyde is produced by preparing 1-chloro-3,3,3-trifluoropropene as a starting material, converting the 1-chloro-3,3,3-trifluoropropene to 3,3,3-trifluoromethyl vinyl ether (hereinafter occasionally just referred to as "vinyl ether") and then hydrolyzing the 3,3,3-trifluoromethyl vinyl ether.

There is a report in U.S. Pat. No. 2,739,987 about the technique for producing a vinyl ether by reacting 1-chloro-3,3,3-trifluoropropene with a chain alcohol (such as methanol) in the presence of a base such as KOH as represented by the formula (a).

[Chem.1]

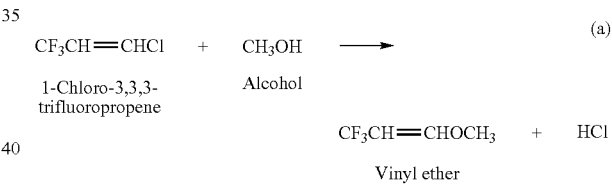

However, the yield of the target 3,3,3-trifluoropropionaldehyde is much lower than 50% when the vinyl ether produced by the above reported process is hydrolyzed in the existence of an inorganic acid such as HCl as the catalyst as represented by the formula (b).

[Chem. 2]

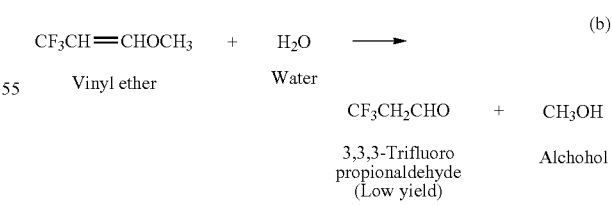

The main cause of such a low product yield is due to the predominant occurrence of a side reaction by which the alcohol by-product of the hydrolysis reacts with the vinyl ether raw material to form an acetal of the 3,3,3-trifluoropropionaldehyde (hereinafter occasionally just referred to as "acetal") as represented by the formula (c).

[Chem. 3]

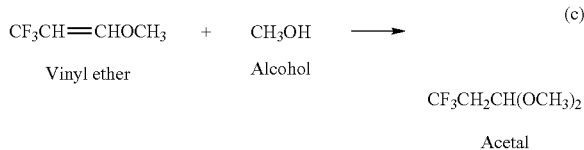

The side reaction (c) becomes more pronounced when the alcohol is used excessively in the vinyl-etherification (a), prior to the hydrolysis (b), and left in the reaction system. This causes a significant decrease in the yield of the target reaction product.

As a solution to the above problem, Patent Publication 5 proposes that the alkane acid of carbon number 3 to 16 coexists as an alcohol acceptor in the reaction system during the hydrolysis of the vinyl ether. Namely, it has been shown that, in the coexistence of the alkane acid of carbon number 3 to 16 during the hydrolysis (b), the by-product alcohol becomes trapped by the alkane acid to allow substantial inhibition of the side reaction (c) so that the yield of the target 3,3,3-trifluoropropionaldehyde from 1-chloro-3,3,3-trifluoropropene can be increased to about 70%.

The process of Patent Publication 5 however requires an equivalent molar amount or an excess amount of the alkane acid with carbon number 3 to 16 as the alcohol acceptor with respect to that of the vinyl ether, which causes a decrease in productivity. In addition, the process of Patent Publication 5 generates an equivalent molar amount or more of alkane acid ester as an undesired by-product with respect to the target 3,3,3-trifluoropropionaldehyde. There is also a drawback that long-chain alkane acid of carbon number 6 or greater (such as hexane acid) is expensive although effective in increasing the yield of the 3,3,3-trifluoropropionaldehyde among various alkane acid compounds.

For these reasons, the conventional production processes of 3,3,3-trifluoropropionaldehyde are still in need of improvements for mass-production applications. There is a demand to develop a more efficient production process of 3,3,3-trifluoropropionaldehyde.

In view of the above problems, the present inventors have made extensive research to develop a suitable process for commercial production of 3,3,3-trifluoropropionaldehyde. As a result of extensive research, the present inventors have found that the above problems can be solved to enable high-yield production of 3,3,3-trifluoropropionaldehyde by: preparing a benzyl vinyl ether of the formula [1] as a starting material and hydrolyzing the benzyl vinyl ether in the presence of a catalyst selected from the group consisting of Arrhenius acids and Lewis acids.

[Chem. 4]

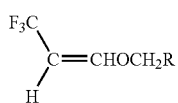

[1]

In the formula [1], R represents phenyl or phenyl having a substituent $R^1$ selected from the group consisting of alkyl groups, alkoxy groups, halogen atoms, nitro groups and amino groups. (Hereinafter, the hydrolysis step of the benzyl vinyl ether may be occasionally referred to as a "second process step").

The present invention is characterized in that the vinyl ether to be hydrolyzed has a functional group with a benzyl structure ($RCH_2$—), where R is the same as above, on the opposite side of the vinyl group from the oxygen atom (—O—). Namely, when the vinyl ether with the benzyl group ($RCH_2$—) is hydrolyzed in the presence of Arrhenius acid or Lewis acid catalyst for production of the target 3,3,3-trifluoropropionaldehyde, no significant amount of acetal is unexpectedly generated by reaction of the by-product benzyl alcohol ($RCH_2OH$) with the benzyl vinyl alcohol raw material as represented below.

[Chem. 5]

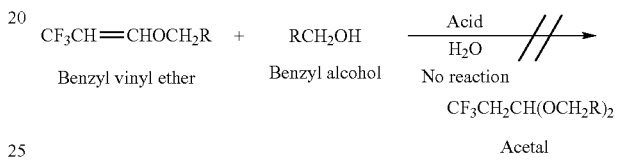

In consequence, it is not necessary to use a large amount of alkane acid with carbon number 3 to 16 as an alcohol acceptor as disclosed in Patent Publication 5. In the present invention, the benzyl vinyl ether is hydrolyzed with only a catalytic amount of Arrhenius acid or Lewis acid to produce the 3,3,3-trifluoropropionaldehyde with a yield much higher than 50%.

The suitable use of low-cost Arrhenius or Lewis acid such as hydrochloric acid, sulfuric acid, iron chloride etc. as the catalyst allows production of the target 3,3,3-trifluoropropionaldehyde with a great economical advantage and high productivity as compared to the process of Patent Publication 5.

The present inventors have also found that the 3,3,3-trifluoropropionaldehyde can be produced smoothly with a high yield by carrying out the hydrolysis reaction of the second process step at a sufficient temperature to distill 3,3,3-trifluoropropionaldehyde and thereby distilling the resulting 3,3,3-trifluoropropionaldehyde continuously or successively in concurrent with the course of the hydrolysis reaction.

The present inventors have confirmed that the benzyl alcohol ($RCH_2OH$) byproduct of the hydrolysis is rarely consumed in the above side reaction and left stably in the reaction system (tank bottom). The benzyl alcohol has a boiling point significantly higher than that of the target 3,3,3-trifluoropropionaldehyde and thus can be efficiently separated and recovered from the reaction system after the completion of the second process step. (The separation/recovery step of the benzyl alcohol ($RCH_2OH$) may be occasionally be referred to as a "third process step" in the present specification.) The benzyl alcohol, after recovered in the third process step, can be used to prepare the next batch of benzyl vinyl ether.

Furthermore, the present inventors have found that the benzyl vinyl ether of the formula [1] can be prepared as the raw material of the second process step (hydrolytic process step), without difficulty, from commercially readily available 1-halogeno-3,3,3-trifluoropropene of the formula [2].

[Chem. 6]

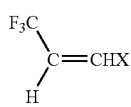
[2]

In the formula [2], X represents halogen (such as fluorine, chlorine, bromine or iodine).

The present inventors have further found that the benzyl vinyl ether (novel compound) of the formula [1] can be produced with a high yield by reacting the 1-halogeno-3,3,3-trifluoropropene of the formula [2] with a benzyl alcohol of the formula [3] in the coexistence of a basic material. (Hereinafter, the production step of the benzyl vinyl ether may be occasionally referred to as a "first process step".)

[Chem. 7]

 [3]

In the formula [3], R represents phenyl or phenyl having a substituent $R^1$ selected from the group consisting of alkyl groups, alkoxy groups, halogen atoms, nitro groups and amino groups.

As the raw material of the first process step, there can be used various kinds of 1-halogeno-3,3,3-trifluoropropene including 1-chloro-3,3,3-trifluoropropene. The 1-chloro-3,3,3-trifluoropropene is also called "HCFC-1233" and refers to either an E-isomer (HCFC-1233t) or a Z-isomer (HCFC-1233c) or a mixture thereof, each of which is commercially available at low cost and suitably usable as the starting material of the first process step.

In this way, the target 3,3,3-trifluoropropionaldehyde can be produced from the low-cost materials advantageously by appropriate combination of the first, second and third process steps.

The present applicant have filed an application (Japanese Patent Application No. 2004-310880) relating to a process for producing 3,3,3-trifluoropropionaldehyde by preparing 1-halogeno-3,3,3-trifluoropropene of the formula [2] as a starting material, forming trifluoromethyl-containing enamine by reaction of the 1-halogeno-3,3,3-trifluoropropene with a cyclic secondary amine, and then, hydrolyzing the trifluoromethyl-containing enamine. This process also has excellent advantages but presents problems that the essential cyclic secondary amine component is expensive and that the cyclic secondary amine cannot be easily recovered from the by-product salt of the cyclic secondary amine. By contrast, the present invention is much more economically advantageous due to the facts that there is no need to use no cyclic secondary amine and the benzyl alcohol can be recovered and reused in the reaction.

The relationship of the first, second and third process steps of the present invention is illustrated in the following scheme.

[Chem. 8]

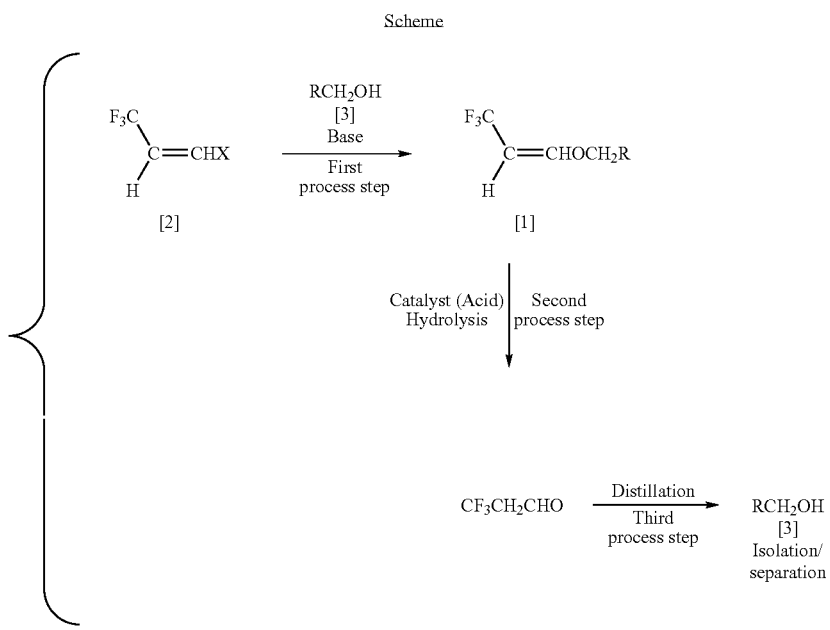

DETAILED DESCRIPTIONS

There is provided according to the present invention a process for producing 3,3,3-trifluoropropionaldehyde from low-cost materials easily in a few steps and with a high yield, thereby enabling commercial-scale production of the 3,3,3-trifluoropropionaldehyde for use as intermediates for medical drugs and agricultural chemicals and as raw materials or synthetic intermediates for high-performance materials such as fluorine-containing polymers.

In the present invention, the 3,3,3-trifluoropropionaldehyde is produced with a yield much higher than 50% by preparing a benzyl vinyl ether of the formula [1] as the starting material and hydrolyzing the benzyl vinyl ether with a catalytic amount of Arrhenius acid or Lewis acid (the second process step). When a benzyl alcohol (RCH$_2$OH) is given as a by-product of the hydrolysis reaction, the benzyl alcohol is recovered with a high yield from the reaction system and used to prepare the next batch of benzyl vinyl ether (the third process step). Further, the benzyl vinyl ether of the formula [1] is easily prepared from low-cost 1-halogeno-3,3,3-trifluoropropene of the formula [2] and benzyl alcohol (the first process step).

The present invention will be described in more detail below.

The benzyl vinyl ether of the formula [1] is prepared as the raw material of the hydrolysis (the second process step) in the present invention. Herein, the functional group R of the benzyl vinyl group is phenyl or phenyl having a substituent $R^1$ (where $R^1$ is selected from alkyl group, alkoxy group, halogen atom and nitro group). The alkyl and alkoxy groups as $R^1$ are preferably those having a carbon number of 1 to 6, such as methyl, ethyl, i-propyl, n-propyl, n-butyl, t-butyl, methoxy, ethoxy, i-propoxy, n-propoxy, n-butoxy and t-butoxy. The halogen atom as $R^1$ is any of fluorine, chlorine, bromine and iodine. The functional group $R^1$ may be of single kind or of plural different kinds. Specific examples of the functional group R are unsubstituted phenyl, o-tolyl, m-tolyl, p-tolyl, 3,5-xylyl, 2-ethylphenyl, 3-ethylphenyl, 4-ethylphenyl, 2-chlorophenyl, 3-chlorophenyl and 4-chlorophenyl.

Among others, the functional group R is preferably unsubstituted phenyl because of its low cost and high reactivity. In other words, the benzyl vinyl ether of the formula [1] is preferably benzyl (3-trifluoromethyl) vinyl ether (1-benzyloxy-3,3,3-trifluoropropene) as represented by the following formula.

[Chem. 9]

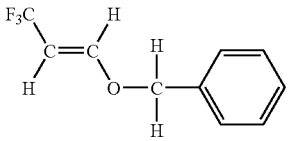

Although the benzyl vinyl ether of the formula [1] can be prepared by any method and used in the second process step, it is particularly preferable to prepare the benzyl vinyl ether of the formula [1] in the first process step using the 1-halogeno-3,3,3-trifluoropropene of the formula [2] as the starting material.

When the benzyl alcohol ($RCH_2OH$) is given as the by-product of the second process step, it is preferable to separate and recover the benzyl alcohol from the reaction system in the third process step after the completion of the second process step.

In the present specification, the first to third process steps will be explained sequentially.

An explanation of the first process step will be given below. The first process step is to prepare the benzyl vinyl ether of the formula [1] by reaction of the 1-halogeno-3,3,3-trifluoropropene of the formula [2] and the benzyl alcohol of the formula [3] in the coexistence of a basic material.

In the 1-halogeno-3,3,3-trifluoropropene of the formula [2], the halogen X is any of fluorine, chlorine, bromine and iodine. It is preferable to use 1-chloro-3,3,3-trifluoropropyene, which corresponds to the case where X is chlorine, due to the fact that the 1-chloro-3,3,3-trifluoropropyene is commercially available as HCFC-1233. The 1-chloro-3,3,3-trifluoropropyene refers to either of an E-isomer (HCFC-1233t) and a Z isomer (HCFC-1233c). These isomers can suitably be used alone or in combination thereof. In the case of using the E-isomer of 1-chloro-3,3,3-trifluoropropyene as the starting material, an E-isomer of the vinyl ether of the formula [1] is given as a main reaction product. In the case of using the Z isomer of 1-chloro-3,3,3-trifluoropropyene as the starting material, a Z isomer of the vinyl ether of the formula [1] is given as a main reaction product.

The benzyl alcohol of the formula [3] is selected corresponding to the kind of the benzyl vinyl ether of the formula [1] as the target product of the first process step. Specific examples of the benzyl alcohol are unsubstituted benzyl alcohol, methylbenzyl alcohol, ethylbenzyl alcohol and chlorobenzyl alcohol. It is particularly preferable to use unsubstituted benzyl alcohol, which is readily available at lowest cost and shows high reactivity in the second process step (hydrolysis).

There is no particular restriction on the amount of the benzyl alcohol used in the first process step. The amount of the benzyl alcohol used is usually 1.0 to 10.0 moles, preferably 1.0 to 7.0 moles, particularly preferably 1.0 to 4.0 moles, per 1.0 mole of the 1-halogeno-3,3,3-trifluoropropene. It is however undesirable that the amount of the benzyl alcohol exceeds 10 moles in terms of productivity and cost efficiency.

In the first process step, the basic material is required to neutralize a hydrogen halide by-product and shift the chemical equilibrium to the reaction product side. In the absence of the basic material, the benzyl vinyl ether of the formula [1] is not significantly prepared. There is no particular restriction on the kind of the basic material. The basic material is preferably an inorganic base. Specific examples of the inorganic base are sodium hydroxide, sodium carbonate, sodium acid carbonate, potassium hydroxide, potassium carbonate, potassium acid carbonate, calcium hydroxide and lithium hydroxide. Among others, preferred are sodium hydroxide and potassium hydroxide, both of which are available at low cost. The reaction proceeds even when the basic material is an organic base (such as methylamine, dimethylamine, trimethylamine, diethylamine, triethylamine, tributylamine, pyridine, piperidine, methylpyridine, dimethylpyridine and aniline). However, the inorganic base is more preferred than the organic base for the reason that the organic base is relatively expensive and requires burdensome purification operation after the reaction. There is no particular restriction on the amount of the basic material used. The amount of the basic material used is preferably 1.0 to 10 moles, preferably 1.0 to 6.0 moles, particularly preferably 1.0 to 4.0 moles, per 1.0 mole of the 1-halogeno-3,3,3-trifluoropropene. There will be no influence on reactivity even if the amount of the basic material exceeds 10 moles. It is however undesirable that the amount of the basic material exceeds 10 moles in terms of productivity and cost efficiency. On the other hand, if the amount of the basic material is less than 1.0 mole, there arises an undesirable problem that the efficiency of conversion to the benzyl vinyl ether becomes lowered so that it is difficult to isolate/purify the benzyl vinyl ether after the completion of the reaction.

In order to increase the solubility of the basic material in the reaction system, water may be added in the first process step. It is generally preferable to add water in the first process step. The amount of water used is preferably 0.01 to 2 g, particularly preferably 0.1 to 1 g, per 1 g of the basic material.

A phase transfer catalyst may also be added in order to accelerate the reaction of the first process step. There is no particular restriction on the kind of the phase transfer catalyst. Crown ethers, quaternary ammonium salts and phosphonium salts are usable as the phase transfer catalyst. Specific examples of the phase transfer catalyst are 18-crown-6-ether, tetrabutylammonium chloride, tetrabutylammonium bromide and tetrabutylphosphonium chloride. There is also no particular restriction on the amount of the phase transfer catalyst used. The amount of the phase transfer catalyst used is usually 0.01 to 30 parts by weight, preferably 0.1 to 15 parts by weight, particularly preferably 0.5 to 10 parts by weight, per 100 parts by weight of the 1-halogeno-3,3,3-trifluoropropene. There will be no influence on reactivity even if the amount of the phase transfer catalyst exceeds 30 parts by weight. It is however undesirable that the amount of the phase transfer catalyst exceeds 30 parts by weight in terms of productivity and cost efficiency. As will be apparent from Example 1, the phase transfer catalyst is not necessarily required in the first process step. There are many cases where the reaction proceeds with sufficient selectivity and rate in the presence of no phase transfer catalyst.

The reaction temperature of the first process step is usually 0 to 200° C., preferably 20 to 150° C., more preferably 30 to 100° C.

The reaction of the first process step can be carried out even in a pressure-resistant reactor such as autoclave, but is generally carried out in the air under atmospheric pressure. As both of the raw material 1-halogeno-3,3,3-trifluoropropene and the target product benzyl vinyl ether are stable in the air, it suffices to carry out the reaction of the first process step in an open air atmosphere.

There is no particular restriction on the reaction time of the first process step. It is preferable to monitor the status of the reaction by e.g. chromatography and finish the reaction upon confirming that the reaction comes close to an end. With this, the reaction mixture containing therein the vinyl ether of the formula [1] is obtained.

The reaction mixture can be used as the starting material of the second process step without purification or after purification for removal of the unreacted raw material and by-product.

In the case of purifying the reaction mixture, there is no particular restriction on the purification technique. It is feasible obtain a mixed organic phase of the vinyl ether and unreacted alcohol by filtrating a solid substance or substances e.g. inorganic salt deposit from the reaction system after the completion of the first process step and subjecting the resulting filtrate to water washing and two-phase separation, or to obtain a mixed fraction of the vinyl ether and unreacted alcohol by filtrating a solid substance or substances e.g. inorganic salt deposit from the reaction system after the completion of the first process step and subjecting the resulting filtrate to simple distillation (crude distillation).

When the benzyl alcohol is used as the alcohol, the acetal formation reaction between the free alcohol and the benzyl vinyl ether during the second process step (hydrolysis) becomes inhibited. There is thus no need to completely remove excess alcohol from the reaction system. It suffices to provide crude purification after the completion of the first process step.

Next, an explanation of the second process step will be given below. The second process step is to hydrolyze the benzyl vinyl ether of the formula [1] in the presence of the catalyst selected from the group consisting of the Arrhenius acids and Lewis acids, thereby producing the target 3,3,3-trifluoropropionaldehyde.

In the second process step, there can be used various kinds of benzyl vinyl ether compound [1]. It is particularly preferable to use 1-benzyloxy-3,3,3-trifluoropropene, which corresponds to the case where R is unsubstituted phenyl.

In terms of cost effectiveness, it is particularly preferable to use the benzyl vinyl ether prepared by the first process step. However, the benzyl vinyl ether is not necessarily prepared by the first process step and can be prepared by any other method for use as the starting material of the second process step.

The catalyst is at least one selected from the Arrhenius acids and Lewis acids. Herein, the Arrhenius acid is a chemical species that has the property of dissociating a proton or protons and generally exhibits a pH of 6 or lower when dissolved in water to a concentration of 0.1 mol·dm³. Preferable examples of the Arrhenius acids are those classed as strong or medium acids, including hydrochloric acid, sulfuric acid, trifluoromethanesulfonic acid, hydrofluoric acid, hydrobromic acid, hydriodic acid, methanesulfonic acid, benzenesulfonic acid, trifluoroacetic acid, phosphoric acid, silicic acid, boric acid, formic acid, acetic acid, propionic acid, butyric acid, valeric acid, pivalic acid, oxalic acid, succinic acid, adipic acid and crotonic acid. Among others, especially preferred are hydrochloric acid and sulfuric acid, both of which are available at low cost and show high catalytic activity. It is not desirable to use strong oxidizing acids such as nitric acid, perchloric acid, chloric acid, permanganic acid and chromic acid due to the fact that these strong oxidizing acids function as the catalyst of the hydrolysis for production of the 3,3,3-trifluoropropionealdehyde, but can cause oxidation of the target reaction product to form 3,3,3-trifluoropropionic acid.

The Lewis acid is a chemical species that has an atom capable of accepting an electron pair in its empty orbit. Transition metal oxides and transition metal complex are usable as the Lewis acids. Specific examples of the Lewis acids are $Ag^+$, $I^+$, $SO_3$, $SO_2$, $BF_3$, $BCl_3$, aluminum chloride ($AlCl_3$), $AlBr_3$, iron (III) chloride ($FeCl_3$), $FeBr_3$, $Fe_2O_3$, FeO, metallocene (ferrocene, cobaltocene, nickelocene etc.), $Cu_2O$, CuO, copper (II) chloride ($CuCl_2$), $SbCl_5$, tin (IV) chloride ($SnCl_4$), titanium chloride ($TiCl_4$), $PdCl_2$ and $Pd(OCOCH_3)_2$. Among others, especially preferred is iron (III) chloride ($FeCl_3$), which is available at low cost and shows high catalytic activity. The above acid catalysts can be used alone or in combination thereof. It is particularly preferable to use a mixed catalyst of iron (III) chloride and hydrochloric acid. In the case of using the mixed catalyst of iron (III) chloride and hydrochloric acid, it is likely that the reaction could proceed under very moderate conditions (relatively low temperature conditions).

The amount of the catalyst used is generally 0.0001 to 0.8 equivalent weight, preferably 0.005 to 0.5 equivalent weight, more preferably 0.01 to 0.3 equivalent weight, with respect to the vinyl ether of the formula [1]. Herein, the term "equivalent weight" is defined as the catalyst mole number divided by the catalyst valance. The catalyst valance means the valence of the acid anion in the Arrhenius acid (e.g. valence 1 for hydrochloric acid and valence 2 for sulfuric acid) or the valence of the atom with an empty orbit in the Lewis acid (e.g. valence 3 for $FeCl_3$, valence 2 for FeO and valence 1 for $Cu_2O$). In the case of using a plurality of catalysts in combination, the total of the equivalent weights of these plural catalysts falls within the above-specified range. In the case of using the transition metal catalyst and the Arrhenius acid catalyst in combination, there is no particular restriction on the ratio between the transition metal catalyst and the Arrhenius acid catalyst. In general, however, the transition metal catalyst is used in a smaller amount as compared to the Arrhenius acid catalyst. One preferable example of such combined catalyst use is 0.01 to 0.5 equivalent weight of the transition metal catalyst with respect to 1 equivalent weight of the Arrhenius acid catalyst.

The amount of water used in the second process step (hydrolysis) is generally 1 to 20 moles, preferably 1 to 20 moles, more preferably 1 to 5 moles, per 1 mole of the benzyl vinyl ether. It is economically disadvantageous in terms of productivity if the water amount exceeds 20 moles. If the water amount is less than 1 mole, there arise undesirable problems that the target reaction is slowed down and dibenzyl ether is likely to be formed as a by-product to cause a decrease in the recovery rate of the benzyl alcohol.

The reaction temperature of the second process step (the temperature of the liquid phase inside the reactor) depends on the kind of the catalyst used and is generally 50 to 150° C., preferably 70 to 130° C. In the case of using strong sulfuric acid as the catalyst, the reaction temperature of the second process step is particularly preferably in the range of 100 to 120° C. In the case of using the mixed catalyst of iron (III) chloride and 30% hydrochloric acid, the reaction temperature of the second process step is particularly preferably in the range of 70 to 100° C. The reaction temperature can be maintained constant throughout the reaction, or can be controlled to a relatively low degree in the initial stage of the reaction and gradually increased in the course of the reaction.

The reaction of the second process step can be carried out under atmospheric pressure, under elevated pressure or under reduced pressure. It is preferable to carry out the reaction of the second process step under atmospheric pressure for greatest ease of the reaction.

The resulting 3,3,3-trifluoropropionaldehyde is relatively stable in the coexistence of water, but upon contact with the air in the presence of the transition metal compound, may become oxidized by oxygen in the air to form 3,3,3-trifluoropropion acid. In the case of using the transition metal catalyst (e.g. $FeCl_3$, $FeBr_3$, $Fe_2O_3$ or $Cu_2O$) in the second process step, it is thus preferable to carry out the hydrolysis reaction in an atmosphere of inert gas (e.g. nitrogen, helium) in order to prevent the 3,3,3-trifluoropropionaldehyde from being oxidized by oxygen. On the other hand, the hydrolysis reaction can be suitably carried out in an inert gas atmosphere or in the air in the case of using Arrhenius acid such as hydrochloric acid or sulfuric acid as the catalyst in the second process step.

There is no particular restriction on the reaction form of the second process step. For ease of reaction control, it is preferable to mix the benzyl vinyl ether of the formula [1] as the starting material, the catalyst and water successively or continuously.

It is particularly preferable to carry out the reaction of the second process step at a temperature sufficient to distill the target 3,3,3-trifluoropropionaldehyde (at least at a temperature higher than or equal to the boiling point of the target product compound) and thereby distill the resulting 3,3,3-trifluoropropionaldehyde continuously or successively in concurrent with the course of the reaction. By this technique, the target 3,3,3-trifluoropropionaldehyde can be not only recovered smoothly during the course of the reaction but also eliminated from the reaction system constantly so as to shift the equilibrium of formation of the 3,3,3-trifluoropropionaldehyde to the target product side and thereby increase the yield of the 3,3,3-trifluoropropionaldehyde to a higher level. At this time, the target 3,3,3-trifluoropropionaldehyde has a boiling point sufficiently lower than those of the benzyl vinyl ether of the formula [1] and the benzyl alcohol of the formula [2] and thus will not form an azeotropic mixture with these compounds [1] and [2].

It is more particularly preferable to carry out the reaction of the second process step in the air at a temperature higher than or equal to the boiling point of 3,3,3-trifluoropropionaldehyde and thereby obtain the resulting 3,3,3-trifluoropropionaldehyde continuously and successively as a fraction of distillate (as will be discussed in Examples 1 to 3).

The amount of the byproduct benzyl alcohol in the reaction system (tank bottom) increases as the hydrolysis of the second process step proceeds. It is however unlikely that the acetal will be formed by reaction between the by-product benzyl alcohol and the unreacted benzyl vinyl ether as already mentioned before. This hydrolytic technique thus does not result in a decrease in the yield of the 3,3,3-trifluoropropionaldehyde.

As an alternative hydrolytic technique, it is reasonably feasible to carry out the reaction of the second process step e.g. under reflux conditions and recover the 3,3,3-trifluoropropionaldehyde by distillation after the completion of the reaction (as will be discussed in Example 4).

There is no particular restriction on the reaction time of the second process step. It is preferable to monitor the status of the reaction by e.g. chromatography and finish the reaction upon confirming that the reaction comes close to an end.

An explanation of the third process step will be next given below. The third process step is to recover the by-product benzyl alcohol by further distillation subsequently after obtaining the 3,3,3-trifluoropropionaldehyde produced in the second process step as the distillate fraction.

The benzyl alcohol can be recovered by, after recovering the 3,3,3-trifluoropropionaldehyde by distillation, heating the distillation residue to a temperature higher than or equal to the point at which the benzyl alcohol gets distilled at normal pressures (i.e. the boiling point of benzyl alcohol: 203 to 205° C.), or heating the distillation residue to the corresponding point under reduced pressure. As already mentioned above, the benzyl alcohol is unlikely to form acetal in the hydrolytic reaction system (i.e. in the presence of water). Thus, the benzyl alcohol can be recovered with a very high yield as will be explained in Examples 1 and 2.

The present invention will be described below in more detail with reference to the following examples. It should be however noted that the following examples are only illustrative and not intended to limit the invention thereto. In the following explanation, all percentages (%) of the product composition are by area as determined by direct gas chromatographic analysis of the reaction product.

EXAMPLE 1

(First process step) A 100-ml stainless steel autoclave was cooled by dry ice and acetone and filled with a solution of 19 g (0.34 mol) KOH in 37.2 g (0.34 mol) benzyl alcohol and 6.2 g water and 22.5 g (0.17 mol) (1Z) 1-chloro-3,3,3-trifluoropropene. The resulting solution was heated to around 22° C., stirred for 1 hour, and then, further stirred under heating at 70° C. for 12 hours. The reaction solution was analyzed by gas chromatography and found to contain 49.5% benzyl alcohol, 0.5% (1Z) 1-chloro-3,3,3-trifluoropropene as the raw material, 45% (1Z) 1-benzyloxy-3,3,3-trifluoropropene and 5.0% (1E) 1-benzyloxy-3,3,3-trifluoropropene.

After filtrating a salt deposit from the reaction solution, the reaction solution was subjected to flash distillation (crude distillation) to obtain 54 g of a mixture of distillate fraction of 90-100° C./2.7 kPa. The mixture was analyzed by gas chromatography and found to contain 49.7% benzyl alcohol, 45.3% (1Z) 1-benzyloxy-3,3,3-trifluoropropene and 5.0% (1E) 1-benzyloxy-3,3,3-trifluoropropene.

(Second process step) The thus-obtained mixture (54 g) was filled into a 100-ml three-neck glass flask with a magnetic stirrer, a thermometer, a distillation column, a condenser tube and a receiver flask, followed by adding thereto 1.3 g (0.07 mol) water and 2.7 g (0.026 mol) 35% hydrochloric acid. The resulting solution was reacted by stirring under heating at a temperature of 100 to 120° C. With this, target 3,3,3-trifluoropropionaldehyde was obtained as a distillate fraction of boiling point 55 to 57° C. (yield amount: 13.8 g, yield rate of second process step: 91.7%, total yield rate of first and second process steps: 71.7%, purity: 99%).

(Third process step) The distillation was further continued to recover benzyl alcohol (recovery amount: 26 g, recovery rate: 70%) after completion of the distillation of the 3,3,3-trifluoropropionaldehyde.

[Property Data]

(1Z) 1-benzyloxy-3,3,3-trifluoropropene:
$^1$H-NMR spectrum (400 MHz, $CDCl_3$) δ (ppm): 4.67 (1H, m), 4.98 (2H, s), 6.38 (1H, d, J=6.8 Hz), 7.35 (5H, m)

$^{19}$F-NMR spectrum (400 MHz, CDCl$_3$, CFCl$_3$) δ (ppm): −57.92 (3F, d, J=6.3 Hz)

(1E) 1 benzyloxy-3,3,3-trifluoropropene:
$^1$H-NMR spectrum (400 MHz, CDCl$_3$) δ (ppm): 4.81 (2H, s), 5.06 (1H, dq, J=12.6, 6.3 Hz), 7.12 (1H, dq, J=12.6, 2.0 Hz), 7.35 (5H, m)
$^{19}$F-NMR spectrum (400 MHz, CDCl$_3$, CFCl$_3$) δ (ppm): −59.81 (3F, d, J=6.3 Hz)

3,3,3-trifluoropropionaldehyde:
$^1$H-NMR spectrum (400 MHz, CDCl$_3$) δ (ppm): 3.62 (3H, s), 4.926 (1H, dq, J=13.2, 6.4 Hz), 7.08 (1H, dq, J=13.2, 2.0 Hz)
$^{19}$F-NMR spectrum (400 MHz, CDCl$_3$, CFCl$_3$) δ (ppm): −59.59 (3F, d, J=6.4 Hz)

EXAMPLE 2

(First process step) A 100 ml stainless steel autoclave was cooled by dry ice and acetone and filled with a solution of 19 g (0.34 mol) KOH in 37.2 g (0.34 mol) benzyl alcohol and 6.2 g water, 22.5 g (0.17 mol) (1Z) 1-chloro-3,3,3-trifluoropropene and 0.56 g 18-crown-6-ether. The resulting solution was heated to around 22° C., stirred for 1 hour, and then, further stirred under heating at 70° C. for 12 hours. The reaction solution was analyzed by gas chromatography and found to contain 50% benzyl alcohol, 44.8% (1Z) 1-benzyloxy-3,3,3-trifluoropropene and 5.2% (1E) 1-benzyloxy-3,3,3-trifluoropropene.

After filtrating a salt deposit from the reaction solution, the reaction solution was subjected to flash distillation (crude distillation) to obtain 53.5 g of a mixture of distillate fraction of 90-100° C./2.7 kPa. The mixture was analyzed by gas chromatography and found to contain 49.9% benzyl alcohol, 44.9% (1Z) 1-benzyloxy-3,3,3-trifluoropropene and 5.2% (1E) 1-benzyloxy-3,3,3-trifluoropropene.

(Second process step) The thus-obtained mixture (53.5 g) was filled into a 100-ml three-neck glass flask with a magnetic stirrer, a thermometer, a distillation column, a condenser tube and a receiver flask, followed by adding thereto 6.2 g (0.34 mol) water and 1.4 g (0.0086 mol) FeCl$_3$. The resulting solution was reacted by stirring under heating at a temperature of 100 to 120° C. With this, target 3,3,3-trifluoropropionaldehyde was obtained as a distillate fraction of boiling point 55 to 57° C. (yield amount: 12 g, yield rate of second process step: 80.8%, total yield rate of first and second process steps: 62.4%, purity: 99%).

(Third process step) The distillation was further continued to recover benzyl alcohol (recovery amount: 31 g, recovery rate: 83%) after completion of the distillation of the 3,3,3-trifluoropropionaldehyde.

EXAMPLE 3

(First process step) A 1000-ml stainless steel autoclave was cooled by dry ice and acetone and filled with a solution of 323 g (5.77 mol) KOH in 415 g (3.84 mol) benzyl alcohol and 138 g water, 500 g (3.83 mol) (1E) 1-chloro-3,3,3-trifluoropropene and 12.5 g tetrabutylammonium. The resulting solution was heated to around 22° C., stirred for 1 hour, and then, further stirred under heating at 80° C. for 24 hours. The reaction solution was analyzed by gas chromatography and found to contain 3.2% benzyl alcohol, 4.2% (1E) 1-chloro-3,3,3-trifluoropropene as the raw material, 86.3% (1E) 1 benzyloxy-3,3,3-trifluoropropene, 4.4% (1Z) 1 benzyloxy-3,3,3-trifluoropropene and 1.3% 1,1,1-trifluoro-3,3-dibenzyloxypropane.

After filtrating a salt deposit from the reaction solution, the reaction solution was subjected to flash distillation (crude distillation) to obtain 643 g of a mixture of distillate fraction of 81-85° C./2 kPa. The mixture was analyzed by gas chromatography and found to contain 2.5% benzyl alcohol, 92.4% (1E) 1-benzyloxy-3,3,3-trifluoropropene, 4.6% (1Z) 1-benzyloxy-3,3,3-trifluoropropene and 0.1% 1,1,1-trifluoro-3,3-dibenzyloxypropane.

(Second process step) The thus-obtained mixture (643 g) was filled into a 1000-ml three-neck glass flask with a magnetic stirrer, a thermometer, a distillation column, a condenser tube and a receiver flask, followed by adding thereto 69 g (3.83 mol) water and 15.5 g (0.155 mol) 98% sulfuric acid. The resulting solution was reacted by stirring under heating at a temperature of 100 to 120° C. With this, target 3,3,3-trifluoropropionaldehyde was obtained as a distillate fraction of boiling point 55 to 57° C. (yield amount: 300 g, yield rate of second process step: 86.8%, total yield rate of first and second process steps: 70%, purity: 99%).

As described above, the isolation yield of the target product of the second process step reached 80.8 to 91.7% when the second process step (hydrolysis) was carried out by successive fractional distillation of 3,3,3-trifluoropropionaldehyde in Examples 1 to 3. When the benzyl alcohol was recovered after the reaction of the second process step in Examples 1 and 2, the benzyl alcohol recovery yield exceeded 80%.

EXAMPLE 4

A mixture (composition: 2.5% benzyl alcohol, 92.7% (1E) 1-benzyloxy-3,3,3-trifluoropropene, 4.7% (1Z) 1-benzyloxy-3,3,3-trifluoropropene and 0.1% 1,1,1-trifluoro-3,3-dibenzyloxypropane) was prepared in the same way as in Example 3. Then, 34 g of the prepared mixture was filled into a 100-ml three-neck glass flask with a magnetic stirrer, a thermometer and a reflux condenser, followed by adding thereto 1.5 g (0.08 mol) water and 0.67 g (0.007 mol) 98% sulfuric acid and stirring the mixture under heating at 100° C. for 2 hours. The resulting reaction solution was analyzed by gas chromatography and found to contain 66.2% target 3,3,3-trifluoropropionaldehyde, 1% (1E) 1-benzyloxy-3,3,3-trifluoropropene, 0.4% (1Z) 1-benzyloxy-3,3,3-trifluoropropene and 1.4% 1,1,1-trifluoro-3,3-dibenzyloxypropane. After replacing the reflux condenser with a distillation column and a receiver flask, the reaction solution was subjected to distillation to obtain the target 3,3,3-trifluoropropionaldehyde as a distillate fraction of boiling point 55 to 57° C. (yield amount: 10 g, yield rate: 53.9%, purity: 99%).

In Example 4, the second process step (hydrolysis) was carried out under reflux conditions and, after the completion of the reaction, the target 3,3,3-trifluoromethylpropionaldehyde was isolated by distillation. The yield of the target product of the second process step was slightly lower in Example 4 than in Examples 1 to 3 but reached about 54%. The 3,3,3-trifluoropropionaldehyde was produced as a main product even by this procedure.

EXAMPLE 5

The first process step was carried out in the same way as in Example 3, thereby preparing a reaction mixture (gas chromatograph composition: 0.4% benzyl alcohol, 89.5% (1E) 1-benzyloxy-3,3,3-trifluoropropene, 5.0% (1Z) 1-benzyloxy-3,3,3-trifluoropropene, 1.8% 1,1,1-trifluoro-3,3-dibenzyloxypropane and 3.3% other compounds). Then, 700 g (3.47 mol) of the prepared mixture was filled into a 1000-ml three-neck glass flask with a magnetic stirrer, a thermometer, a distillation column, a condenser tube and a receiver flask, followed by cooling the mixture to 5° C.

After substituting the inside of the reaction chamber with nitrogen gas, a solution of 72.3 g (0.694 mol, 0.2 equivalent weight) 35% aqueous hydrochloric acid and 5.7 g (0.0347 mol, 0.01 equivalent weight) iron (II) chloride was added to the mixture with caution against heat generation. The resulting mixed solution was stirred for 15 minutes and reacted by stirring under heating at 70 to 100° C. in the nitrogen gas atmosphere. With this, 399 g target 3,3,3-trifluoropropionaldehyde was obtained as a distillate fraction of boiling point 55 to 57° C. (purity: 98%). The yield of the target product of the second process step was 90.4%.

What is claimed is:

1. A process for producing 3,3,3-trifluoropropionaldehyde, comprising:
    hydrolyzing a benzyl vinyl ether of the formula [1] in the presence of a catalyst selected from the group consisting of Arrhenius acids and Lewis acids,

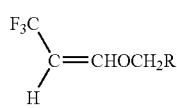
[1]

where R represents phenyl or phenyl having a substituent $R^1$ selected from the group consisting of alkyl groups, alkoxy groups, halogen atoms, nitro groups and amino groups.

2. The process for producing 3,3,3-trifluoropropionaldehyde according to claim 1, wherein R represents phenyl.

3. The process for producing 3,3,3-trifluoropropionaldehyde according to claim 1, wherein the catalyst is selected from the group consisting of sulfuric acid, hydrochloric acid, iron (III) chloride, copper (II) chloride, aluminum chloride, tin (IV) chloride and titanium chloride.

4. The process for producing 3,3,3-trifluoropropionaldehyde according to claim 1, wherein the catalyst has an equivalent weight of 0.005 to 0.5 with respect to the benzyl vinyl ether of the formula [1].

5. The process for producing 3,3,3-trifluoropropionaldehyde according to claim 1, wherein said hydrolizing is carried out at a sufficient temperature to distill 3,3,3-trifluoropropionaldehyde so as to distill the 3,3,3-trifluoropropionaldehyde continuously or successively in concurrent with the course of said hydrolyizing.

6. The process for producing 3,3,3-trifluoropropionaldehyde according to claim 1, wherein the benzyl vinyl ether of the formula [1] is prepared by reacting 1-halogeno-3,3,3-trifluoropropene of the formula [2] with benzyl alcohol of the formula [3] in the presence of a basic material,

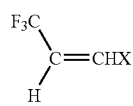
[2]

where X represents halogen selected from the group consisting of fluorine, chlorine, bromine and iodine; and

RCH$_2$OH
[3]

where R represents phenyl or phenyl having a substituent $R^1$ selected from the group consisting of alkyl groups, alkoxy groups, halogen atoms, nitro groups and amino groups.

7. The process for producing 3,3,3-trifluoropropionaldehyde according to claim 1, wherein the benzyl alcohol of the formula [3] is recovered by distilling a residue after distilling the 3,3,3-trifluoropropionaldehyde out of a reaction mixture resulting from said hydrolyzing.

8. A process for producing 3,3,3-trifluoropropionaldehyde, comprising:
    a first step of preparing a benzyl vinyl ether of the formula [1] by reacting 1-halogeno-3,3,3-trifluoropropene of the formula [2] with benzyl alcohol of the formula [3] in the presence of a basic material,

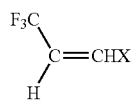
[2]

where X represents halogen selected from the group consisting of fluorine, chlorine, bromine and iodine,

RCH$_2$OH
[3]

where R represents phenyl or phenyl having a substituent $R^1$ selected from the group consisting of alkyl groups, alkoxy groups, halogen atoms, nitro groups and amino groups,

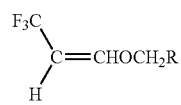
[1]

where R represents phenyl or phenyl having a substituent $R^1$ selected from the group consisting of alkyl groups, alkoxy groups, halogen atoms, nitro groups and amino groups;
    a second step of obtaining a reaction mixture of 3,3,3-trifluoropropionaldehyde by hydrolyzing the benzyl vinyl ether of the formula [1] in the presence of a catalyst selected from the group consisting of Arrhenius acids and Lewis acids and having an equivalent weight of 0.005 to 0.5 with respect to the benzyl vinyl ether; and
    a third step of recovering the benzyl alcohol of the formula [3] by distilling a residue after distilling off the 3,3,3-trifluoropropionaldehyde from the reaction mixture.

9. A benzyl vinyl ether represented by the formula [1]

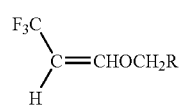
[1]

where R represents phenyl or phenyl having a substituent $R^1$ selected from the group consisting of alkyl groups, alkoxy groups, halogen atoms, nitro groups and amino groups.

* * * * *